United States Patent
Misumi et al.

(10) Patent No.: US 11,707,521 B2
(45) Date of Patent: Jul. 25, 2023

(54) MUCOSAL ADJUVANT

(71) Applicants: DENKA COMPANY LIMITED, Chuo-ku (JP); NATIONAL UNIVERSITY CORPORATION KUMAMOTO UNIVERSITY, Kumamoto (JP)

(72) Inventors: Shogo Misumi, Kumamoto (JP); Naoki Kishimoto, Kumamoto (JP); Ryotaro Mitsumata, Gosen (JP); Nagisa Nakata, Gosen (JP); Takuma Gotanda, Gosen (JP)

(73) Assignees: DENKA COMPANY LIMITED, Tokyo (JP); NATIONAL UNIVERSITY CORPORATION KUMAMOTO UNIVERSITY, Kumamoto (JP)

( * ) Notice: Subject to any disclaimer, the term of this patent is extended or adjusted under 35 U.S.C. 154(b) by 0 days.

(21) Appl. No.: 17/279,850

(22) PCT Filed: Sep. 26, 2019

(86) PCT No.: PCT/JP2019/037885
§ 371 (c)(1),
(2) Date: Mar. 25, 2021

(87) PCT Pub. No.: WO2020/067302
PCT Pub. Date: Apr. 2, 2020

(65) Prior Publication Data
US 2022/0031838 A1    Feb. 3, 2022

(30) Foreign Application Priority Data

Sep. 26, 2018 (JP) .................. 2018-181040

(51) Int. Cl.
| | | |
|---|---|---|
| A61K 39/39 | (2006.01) | |
| A61K 39/145 | (2006.01) | |
| A61K 9/00 | (2006.01) | |
| A61K 39/00 | (2006.01) | |

(52) U.S. Cl.
CPC ............ *A61K 39/39* (2013.01); *A61K 9/0043* (2013.01); *A61K 39/145* (2013.01); *A61K 2039/525* (2013.01); *A61K 2039/55516* (2013.01)

(58) Field of Classification Search
CPC ........... A61K 2039/55505; A61K 2039/55511; A61K 2039/575; A61K 39/12; A61K 2039/5252; A61K 2039/543; A61K 2039/55516; A61K 39/145; A61K 9/0043; A61K 2039/541; A61P 31/16; A61P 37/04; A61P 43/00; C12N 2760/16134; C12N 2760/16234

See application file for complete search history.

(56) References Cited

U.S. PATENT DOCUMENTS

| | | |
|---|---|---|
| 2007/0219149 A1 | 9/2007 | Hasegawa et al. |
| 2015/0024001 A1 | 1/2015 | Misumi et al. |
| 2017/0196970 A1 | 7/2017 | Jonai et al. |

FOREIGN PATENT DOCUMENTS

| | | |
|---|---|---|
| EP | 2 745 844 A1 | 6/2014 |
| JP | 2005-274366 A | 10/2005 |
| JP | 2013-35817 A | 2/2013 |

OTHER PUBLICATIONS

Extended European Search Report dated May 18, 2022, in corresponding European Patent Application No. 19865238.0, 9 pages.
Yasuharu Otsubo, et al., "Bovine alpha-2-HS-glycoprotein functions as a booster antigen for efficiently stimulating humoral immune responses to CCR5 and SIVmac239 envelope glycoprotein", Biochemical and Biophysical Research Communications, vol. 443, No. 1, Dec. 2, 2013, pp. 301-307.
International Search Report dated Nov. 19, 2019 in PCT/JP2019/037885, 2 pages.
Misumi, S., et al., "Targeted Dell very of Immunogen to Primate M Cells with Tetragalloyl Lysine Dendrimer", The Journal of Immunology, 2009, vol. 182, No. 10, pp. 6061-6070 with cover page.
Xu-Amano, J., et al., "Helper T Cell Subsets for Immunoglobulin A Responses: Oral Immunization with Tetanus Toxoid and Cholera Toxin as Adjuvant Selectively Induces Th2 Cells in Mucosa Associated Tissues", J. Exp. Med., Oct. 1993, vol. 178 (4) pp. 1309-1320.
Takahashi, I., et al., "Mechanisms for Mucosal Immunogenicity and Adjuvancy of *Escherichla coli* Labile Enterotoxin", J. Infect. Dis., 1996, vol. 173 (3), pp. 627-635.
Ainai, A., et al., "Intranasal vaccination with an inactivated whole Influenza virus vaccine induces strong antibody responses in serum and nasal mucus of healthy adults", Human vaccines & immunotherapeutics. 2013, vol. 9 (9), pp. 1962-1970 with cover page.
Peter Parham, "Essential Immunology 2nd Edition", Medical Sciences International, Ltd., 2010, pp. 434-436, (MEDSi)(Japanese translation supervised by Takehiko Sasazuki).
Decision of Refusal issued on Feb. 14, 2023, for Japanese Patent Application No. 2018-181040, 7 pages (with a machine translation).

*Primary Examiner* — Bao Q Li
(74) *Attorney, Agent, or Firm* — Oblon, McClelland, Maier & Neustadt, L.L.P.

(57) ABSTRACT

A mucosal adjuvant may have high mucosal immunogenicity and high safety and be useful in the preparation of mucosal vaccines, and a mucosal vaccine composition may include the same. Such mucosal adjuvant may include TGDK. A method for preparing the mucosal vaccine composition may include mixing TGDK with an immunogen.

8 Claims, 4 Drawing Sheets

MUCOSAL ADJUVANT

TECHNICAL FIELD

The present invention relates to a mucosal adjuvant which enhances the mucosal immunity induction of an antigen.

BACKGROUND ART

Mucosal vaccines initiate both mucosal local immunity and systemic immune response by the transmucosal (e.g., transnasal) administration of antigens, and can thereby construct double defense lines against pathogens. On the other hand, mucosal vaccines practically used are live vaccines having infectiveness or vaccines based on mucosotropic special toxins as antigens. Other inactivated antigens cannot induce sufficient immunity by single administration and need to be combined with adjuvants or the like.

Heretofore, attenuated pathogens having infectiveness have been used as methods for initiating sufficient immunity with mucosal vaccines. However, attenuated live vaccines cause strong side reaction because of having infectiveness. For example, vaccine-associated paralytic polio of oral live polio vaccines is inevitable side reaction, albeit being rare, and reportedly develops due to the reversion of vaccine strains to neurovirulent ones. Thus, inactivated antigens having high safety should also be used in mucosal vaccines. However, it is difficult to confer sufficient immunity by the transmucosal administration of antigens except for antigens such as special toxins. In order to mend this problem, the addition of mucosal adjuvants is possible. Cholera toxin and heat-labile toxin (LT) of enterotoxigenic *E. coli* are known as typical mucosal adjuvants (Non Patent Literatures 1 and 2).

However, the transnasal administration of LT caused facial nerve paralysis (Bell paralysis) in past clinical trials. Thus, use of toxins themselves as adjuvants has been recognized as being problematic in terms of safety. In addition, double-stranded RNA (poly I:C) (Patent Literature 1) also has mucosal adjuvant activity, but, has not yet been put into practical use because of the induction of inflammation or cytokine storm.

For the recent development of transnasal administration influenza vaccines in Japan, clinical trials have been conducted using not split antigens which are antigens for commercially available influenza HA vaccines but inactivated whole particles having higher immunogenicity as antigens (Non Patent Literature 3). This is because the split antigens cannot induce sufficient immune response by transmucosal administration. However, the inactivated whole-virus antigens have side reaction problems (local reaction of administration sites and the onset of fever), particularly, in children, by subcutaneous administration, and currently are not distributed in the market. Thus, it is desirable that use of the split antigens having high safety can achieve immunity induction at substantially the same level as that of the inactivated whole-virus antigens.

Tetragalloyl-D-lysine dendrimer (TGDK) is a molecule specifically binding to a microfold cell (M cell), an antigen sampling cell present in the mucosa (Non Patent Literature 4). Thus, the chemical binding of TGDK to antigens or the like enables vaccine antigens to be efficiently delivered to M cells and can improve immune response. For example, Patent Literature 2 discloses that TGDK-$CH_2$—$CH_2$—$NH_2$ binds to a peptide, a protein, a lipid, a polyethylene glycol or a sugar via a peptide bond or a Schiff base, etc. and can thereby be used as an intestinal immunostimulant. Patent Literature 3 discloses that a covalent conjugate of a Hub antigen, TGDK, and fetuin is capable of serving as a molecular mimic mucosal vaccine of HIV/AIDS.

However, it is totally unknown that the TGDK molecule itself has mucosal adjuvant activity.

CITATION LIST

Patent Literature

Patent Literature 1: JP-A-2005-97267
Patent Literature 2: WO 2007/052641
Patent Literature 3: WO 2013/024859

Non Patent Literature

Non Patent Literature 1: Xu-Amano, J., H. Kiyono, R. J. Jackson, H. F. Staats, K. Fujihashi, P. D. Burrows, C. O. Elson, S. Pillai, J. R. McGhee. 1993. Helper T cell subsets for immunoglobulin A responses: oral immunization with tetanus toxoid and cholera toxin as adjuvant selectively induces Th2 cells in mucosa associated tissues. J. Exp. Med. 1993; 178 (4): 1309-20

Non Patent Literature 2: Takahashi, I., M. Marinaro, H. Kiyono, R. J. Jackson, I. Nakagawa, K. Fujihashi, S. Hamada, J. D. Clements, K. L. Bost, J. R. McGhee. 1996. Mechanisms for mucosal immunogenicity and adjuvancy of *Escherichia coli* labile enterotoxin. J. Infect. Dis. 1996; 173 (3): 627-35

Non Patent Literature 3: Ainai A, Tamura S, Suzuki T, van Riet E, Ito R, Odagiri T, et al., Intranasal vaccination with an inactivated whole influenza virus vaccine induces strong antibody responses in serum and nasal mucus of healthy adults. Human vaccines & immunotherapeutics. 2013; 9 (9): 1962-70

Non Patent Literature 4: Misumi S, Masuyama M, Takamune N, et al., Targeted Delivery of Immunogen to Primate M Cells with Tetragalloyl Lysine Dendrimer Journal of Immunology, 2009; 182 (10): 6061-6070

SUMMARY OF INVENTION

Technical Problem

The present invention relates to a provision of a mucosal adjuvant which has high mucosal immunogenicity and high safety and is useful in the preparation of mucosal vaccines, and a mucosal vaccine composition comprising the same.

Solution to Problem

The present inventors have conducted diligent studies in light of the problems described above, and consequently found that TGDK, which has heretofore been chemically bound to a vaccine antigen and used for delivering the antigen to M cells, unexpectedly has adjuvant activity in itself and can enhance the ability of the antigen to induce mucosal immunity.

Specifically, the present invention relates to the following 1) to 10).

1) A mucosal adjuvant comprising TGDK.
2) A mucosal adjuvant composition comprising TGDK and a pharmaceutically acceptable carrier.
3) A mucosal vaccine composition comprising a mucosal adjuvant according to 1) and an immunogen.

4) The mucosal vaccine composition according to 3), wherein the immunogen is whole particles or a split antigen of influenza virus.

5) A method for preparing a mucosal vaccine composition according to 3) or 4), comprising mixing TGDK with an immunogen.

6) TGDK for use as a mucosal adjuvant.

7) A composition comprising TGDK and an immunogen, for use in mucosal vaccine therapy.

8) Use of TGDK for producing a mucosal adjuvant. 9) Use of a composition comprising TGDK and an immunogen for producing a mucosal vaccine.

10) Mucosal vaccine therapy comprising administering a composition comprising TGDK and an immunogen to a subject in need thereof.

Advantageous Effects of Invention

The mucosal adjuvant of the present invention enables mucosal vaccines to be prepared using safe inactivated antigens. Mucosal vaccines using split antigens having higher safety can be provided, as in, for example, currently distributed influenza HA vaccines. Such mucosal vaccines can make a great contribution as prophylactic drugs to the medical industry.

DESCRIPTION OF EMBODIMENTS

Figure 1:
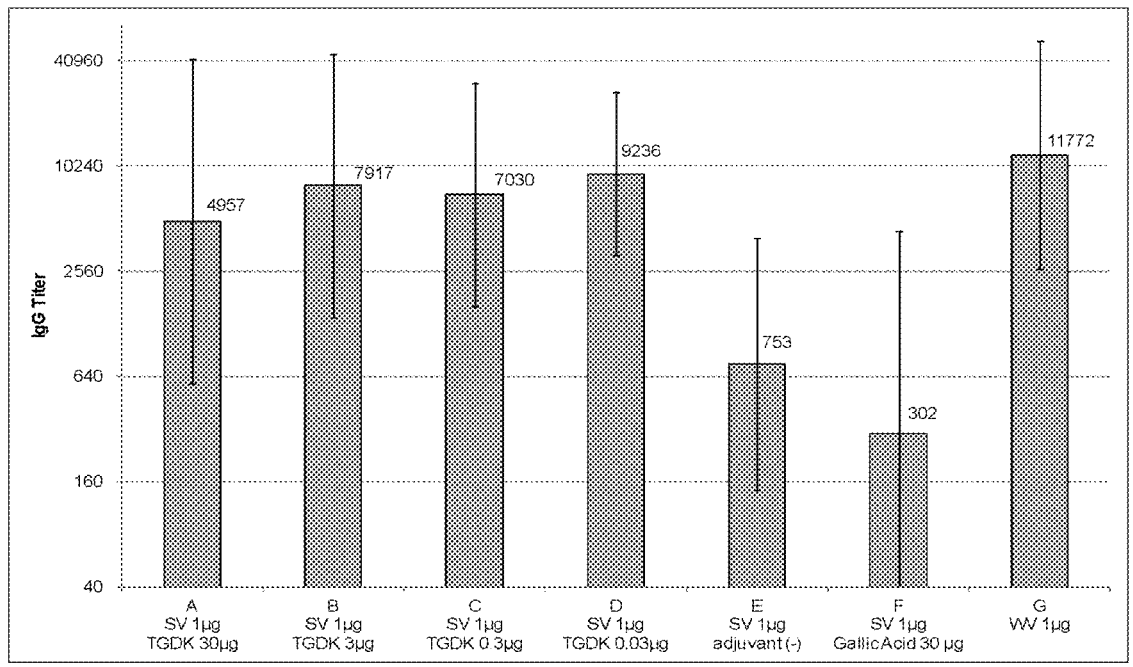
FIG. 1 shows the A/California/07/2009 strain-specific IgG antibody titer of a split antigen administration group.

In the present invention, the term "TGDK" is an abbreviation of tetragalloyl-D-lysine dendrimer and refers to N2,N6-bis[N2,N6-bis(3,4,5-trihydroxybenzoyl)-lysyl]-N-(2-aminoethyl)-lysinamide. TGDK is known as a target molecule of M cells, antigen sampling cells present in the mucosa.

TGDK can be produced, for example, by use of a tetragalloyl-D-trilysinyl diethylamine solid-phase method using gallic acid and D-lysine (see Non Patent Literature 4 described above).

As shown in Examples described later, in the case of mucosally administering a vaccine composition prepared by mixing an influenza vaccine strain (a split antigen/an inactivated whole-virus antigen) with TGDK to mice, the titer of induced IgG specifically binding to the antigen is significantly higher than that for a TGDK non-addition group. In the case of inducing immunity with the split antigen added with TGDK, an IgG titer is obtained at substantially the same level as in the case of inducing immunity using the inactivated whole-virus antigen alone. As for the geometric mean titers (GMT) of IgG1 and IgG2a, GMT is markedly elevated in IgG2a excellent in the ability to defend against infection with influenza virus.

Specifically, TGDK has mucosal adjuvant activity of enhancing the antibody-inducing ability in case of the mucosal administration of an immunogen (antigen). Accordingly, TGDK can serve as a mucosal adjuvant. A composition containing TGDK and a pharmaceutically acceptable carrier can serve as a mucosal adjuvant composition. TGDK can also be used for producing a mucosal adjuvant or a mucosal adjuvant composition.

In the present invention, the term "mucosal adjuvant" means a substance increasing immune response to an immunogen when the immunogen is mucosally administered.

In this context, the term "mucosal administration" refers to an administration mode via the mucosa. The "mucosa" refers to an internal wall of, particularly, a hollow organ which communicates with the outside, such as the digestive organ, the respiratory organ, the urogenital organ, or the eye, in vertebrates. Thus, examples of such mucosal administration include, but are not limited to, nasal administration (transnasal administration), oral administration, intravaginal administration, upper airway administration, alveolar administration, and eye drop administration.

The mucosal adjuvant or the mucosal adjuvant composition of the present invention can be mucosally administered in combination with an immunogen. The administration may be performed concurrently with administration of the immunogen or may be performed before or after administration of the immunogen.

The dose of the mucosal adjuvant or the mucosal adjuvant composition of the present invention can be appropriately determined according to a subject, an administration method, an administration mode, and the type of an antigen substance.

The mucosal adjuvant of the present invention can be provided as a mucosal vaccine composition in combination with an immunogen. The mucosal vaccine composition of the present invention can be prepared by mixing an immunogen with TGDK, and further can be provided as an appropriate preparation by appropriately adding a pharmaceutically acceptable carrier. In the mucosal vaccine composition of the present invention, TGDK is not in a state chemically bound to the immunogen or other components and is present in a free molecular state.

Examples of the "immunogen" (antigen) include a pathogen of transmucosal infection (e.g., viruses and pathogenic bacteria) and a natural product purified from the pathogen, and a protein, peptide, and polysaccharide artificially prepared by approaches such as gene recombination, specifically, a virion which is a complete virus particle, incomplete virus particles, virion-constituting particle, virus non-structural protein, pathogenic bacteria-derived protein and glycoprotein, protective antigen, and epitope for neutralization reaction. The immunogen includes both one having infectivity and one lacking infectivity (inactivated antigen). Examples of the inactivated antigen include, but are not limited to, an antigen inactivated by physical (e.g., X ray irradiation, heat, and ultrasound) or chemical (formalin, mercury, alcohols, chlorine) operation. The immunogen derived from the pathogen of transmucosal infection is desirably an inactivated antigen derived from the virus or the pathogenic bacteria described above from the viewpoint of safety.

Examples of the virus include chickenpox virus, measles virus, mumps virus, poliovirus, rotavirus, influenza virus, adenovirus, herpesvirus, severe acute respiratory syndrome (SARS) virus, human immunodeficiency virus (HIV), human papillomavirus, and rubella virus. The virus is preferably influenza virus or human immunodeficiency virus, more preferably influenza virus. A whole particle virus may be used as the influenza virus. In the present invention, a split antigen can be used, which is obtained by disrupting virus particles and removing lipids in envelopes.

Examples of the pathogenic bacteria include *Bordetella pertussis, Neisseria meningitidis, Haemophilus influenzae* type b, pneumococcal bacteria, *Mycobacterium tuberculosis, Vibrio cholerae*, and *Corynebacterium diphtheriae*.

Examples of the dosage form of the mucosal vaccine composition include a solution, suspension, and powder.

Examples of the solution include an agent dissolved in purified water, a buffer solution or the like. Examples of the suspension include an agent suspended in purified water, a buffer solution or the like, together with methylcellulose, hydroxymethylcellulose, polyvinylpyrrolidone, gelatin, casein, or the like. Examples of the powder include an agent well mixed with methylcellulose, hydroxymethylcellulose, hydroxypropylmethylcellulose, or the like.

These preparations can be supplemented, if necessary, with an absorption promoter, a surfactant, a preservative, a stabilizer, a moisture proofing agent, a moisturizing agent, a solubilizer, etc. usually used.

The mucosal vaccine composition of the present invention may contain an adjuvant other than TGDK as long as it does not impair the immunogenicity and safety of the vaccine.

The amount of the immunogen contained in the mucosal vaccine composition of the present invention is not particularly limited as long as the amount is sufficient for producing antigen-specific IgG. The amount can be appropriately set in consideration of a ratio to TGDK used in combination therewith. For example, in the case of using a split antigen of influenza virus as the antigen, the split antigen may be contained in a range from 1 to 60 µg of HA (based on HA) more preferably from 9 to 15 µg of HA (based on HA), which is a single dose. The concentration is a value obtained by measuring the concentration of the HA protein through a testing method stipulated by WHO or national standards, such as a single radial immunodiffusion testing method or an HA content method.

The content of TGDK in the mucosal vaccine composition may be appropriately adjusted in consideration of an antibody titer. TGDK may be contained in a range, for example, from 0.03 to 30 µg, more preferably from 0.03 to 0.3 µg, which is a single dose.

The administration route of the vaccine composition of the present invention is not particularly limited. Oral administration or parenteral administration (e.g., nasal administration and eye drop administration) may be used. The vaccine composition of the present invention is administered by, for example, dropping, nebulizing or spraying into the nasal cavity or the oral cavity.

Examples of the subject of the adjuvant composition or the vaccine composition of the present invention include humans and non-human mammals. A human is preferred. Examples of the non-human mammal include mice, rats, hamsters, guinea pigs, rabbits, pigs, cattle, goats, horses, sheep, dogs, cats, monkeys, orangutans, and chimpanzees.

EXAMPLES

Hereinafter, the present invention will be described in more detail with reference to Examples. However, the present invention is not limited by these examples.

Example 1

(1) Each stock solution of influenza HA vaccine "SEIKEN" A/H1N1 subtype (A/California/07/2009 strain) and B/Yamagata lineage (B/Texas/2/2013 strain) was used as a split antigen. These split antigens were mixed and combined such that the amount of hemagglutinin of each strain was 1 µg per 10 µL. TGDK was added thereto to have a final concentration of 0.03 to 30 µg/10 µL. For controls, an adjuvant-non-added dosing solution and a dosing solution added with gallic acid (control of TGDK) to have 30 µg/10 µL were also prepared (Table 1) because TGDK is a substance composed of 4 molecules of gallic acid bound to primary amine of a skeleton formed by 3 molecules of lysine. As in the split antigens, inactivated whole-virus antigens of A/H1N1 subtype (A/California/07/2009 strain) and B/Yamagata lineage (B/Texas/2/2013 strain) were mixed and combined such that the amount of hemagglutinin of each strain was 1 µg per 10 µL. Each dosing solution of the inactivated whole-virus antigens was prepared so as to contain 0.03 or 0.3 µg of TGDK or 30 µg of gallic acid (Table 1).

The preparation of the inactivated whole-virus antigens used in this Example is as described below. The virus was inoculated into the chorioallantoic cavity of a 12 day-old embryonated chicken egg and cultured for 2 days. Then, chorioallantoic fluid was collected. The collected chorioallantoic fluid was clarified by filter filtration and then adsorbed on barium sulfate, and eluted with 12% sodium citrate solution to collect influenza virus. The solution of collected virus was replaced with 6.7 mM phosphate-buffered saline (pH 7.2) by ultrafiltration. After replacement of buffer, a fraction containing the influenza virus was collected by sucrose density gradient centrifugation to thereby complete purification. To this purified influenza virus, beta-propiolactone as an inactivating agent was added to have a final concentration of 0.05% followed by allowing the mixture to react at 4° C. for 24 hours to inactivate the infectivity of the influenza virus. After this inactivation reaction, the buffer was replaced with 6.7 mM phosphate-buffered saline containing 1 w/w % sucrose (pH 7.2) by ultrafiltration (MWCO: 100,000). The resultant was used as an inactivated whole-virus vaccine.

(2) Each dosing solution (Table 1) prepared as described above was administered at a dose of 5 µL per nasal cavity (10 µL in total) to BALB/c mice (female, 5 week-old) (8 animals per group) twice at a 3 week-interval. Two weeks after the second administration, whole blood was collected. Blood serum was prepared by centrifugation. The titer of IgG (total IgG) specifically binding to the A/California/07/2009 strain and the B/Texas/2/2013 strain was measured in the serum. The respective titers of IgG subclass IgG1 and IgG2a were measured as B/Texas/2/2013 strain-specific antibody titers for the serum of an adjuvant non-addition group and a TGDK 0.3 µg addition group of the split antigens and the inactivated whole-virus antigens.

TABLE 1

| # | Antigen Type/subtype and lineage | Strain | Type of antigen | Dose (μg HA/ strain/shot) | Adjuvant name | Adjuvant Dose (μg/Shot) | Administration route |
|---|---|---|---|---|---|---|---|
| A | A/H1N1 B/Victoria | A/California/07/2009 B/Texas/2/2013 | Split | 1 | TGDK | 30 | Transnasal |
| B | A/H1N1 B/Victoria | A/California/07/2009 B/Texas/2/2013 | Split | 1 | TGDK | 3 | Transnasal |
| C | A/H1N1 B/Victoria | A/California/07/2009 B/Texas/2/2013 | Split | 1 | TGDK | 0.3 | Transnasal |
| D | A/H1N1 B/Victoria | A/California/07/2009 B/Texas/2/2013 | Split | 1 | TGDK | 0.03 | Transnasal |
| E | A/H1N1 B/Victoria | A/California/07/2009 B/Texas/2/2013 | Split | 1 | — | — | Transnasal |
| F | A/H1N1 B/Victoria | A/California/07/2009 B/Texas/2/2013 | Split | 1 | Gallic acid | 30 | Transnasal |
| G | A/H1N1 B/Victoria | A/California/07/2009 B/Texas/2/2013 | Whole particles | 1 | — | — | Transnasal |
| H | A/H1N1 B/Victoria | A/California/07/2009 B/Texas/2/2013 | Whole particles | 1 | TGDK | 0.3 | Transnasal |
| I | A/H1N1 B/Victoria | A/California/07/2009 B/Texas/2/2013 | Whole particles | 1 | TGDK | 0.03 | Transnasal |
| J | A/H1N1 B/Victoria | A/California/07/2009 B/Texas/2/2013 | Whole particles | 1 | Gallic acid | 30 | Transnasal |

Figure 2:
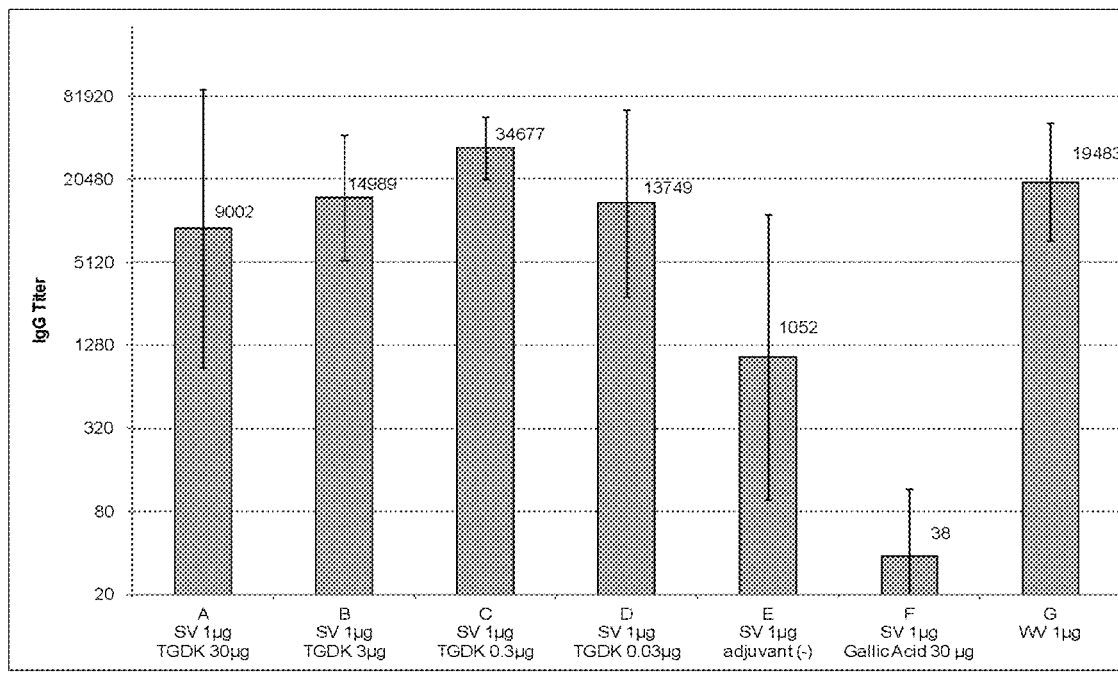
FIG. 2 shows the B/Texas/2/2013 strain-specific IgG antibody titer of a split antigen administration group.

(3) The IgG titers of split antigen administration groups (A to F) and an adjuvant non-addition inactivated whole-virus antigen administration group (G) are as shown in FIGS. 1 and 2. The addition of 0.03 to 30 μg of TGDK per dose to the split antigens elevated an antigen-specific IgG titer in blood for both the strains, as compared with adjuvant non-addition. This IgG titer was at substantially the same level as in the inactivated whole-virus antigens. Particularly, the IgG titer for the A/California/07/2009 strain in the groups added with 0.03 to 0.3 μg of TGDK, and the IgG titer for the B/Texas/2/2013 strain in the groups added with 0.03 to 3 μg of TGDK were significantly higher as compared with those for adjuvant non-addition (Mann-Whitney U test, $p<0.05$). When gallic acid was added to the split antigens, the IgG titer for the A/California/07/2009 strain was at substantially the same level as in adjuvant non-addition, whereas the IgG titer for the B/Texas/2/2013 strain was significantly decreased as compared with adjuvant non-addition. Polyphenol reportedly has an antioxidative effect or an effect of stimulating immunity. In this Example, monomolecular gallic acid does not have adjuvant activity of enhancing antibody induction. This suggested that the structure of TGDK composed of 4 molecules of gallic acid bound to primary amine of a skeleton formed by 3 molecules of lysine is important for exerting adjuvant activity.

Figure 3:
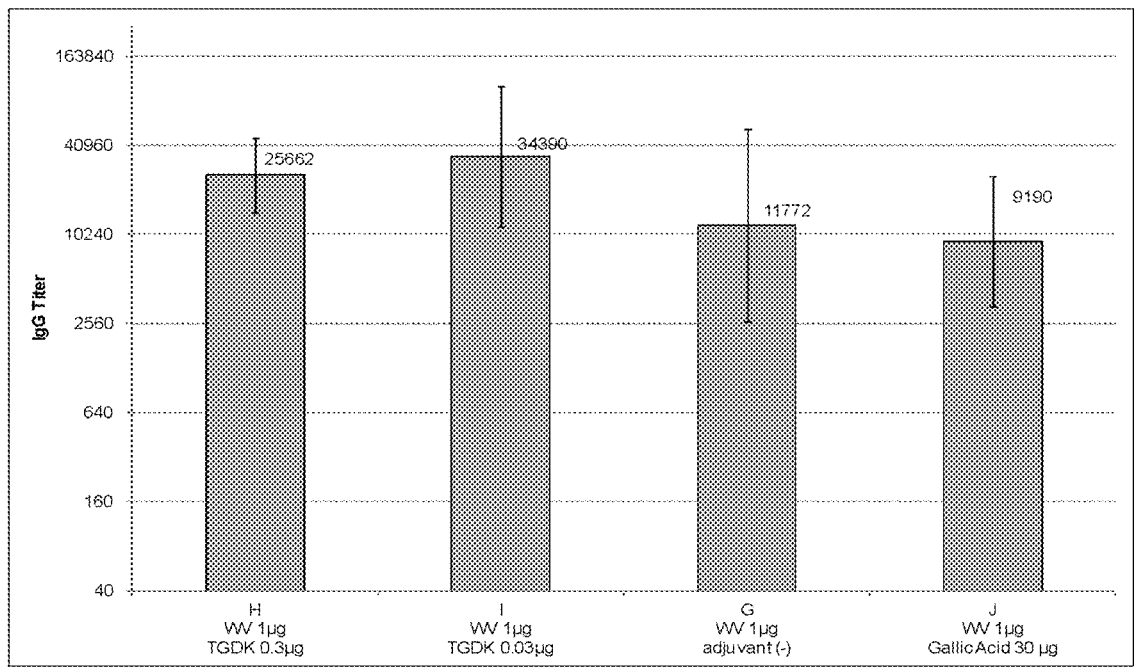
FIG. 3 shows the A/California/07/2009 strain-specific IgG antibody titer of an inactivated whole-virus antigen administration group.
Figure 4:
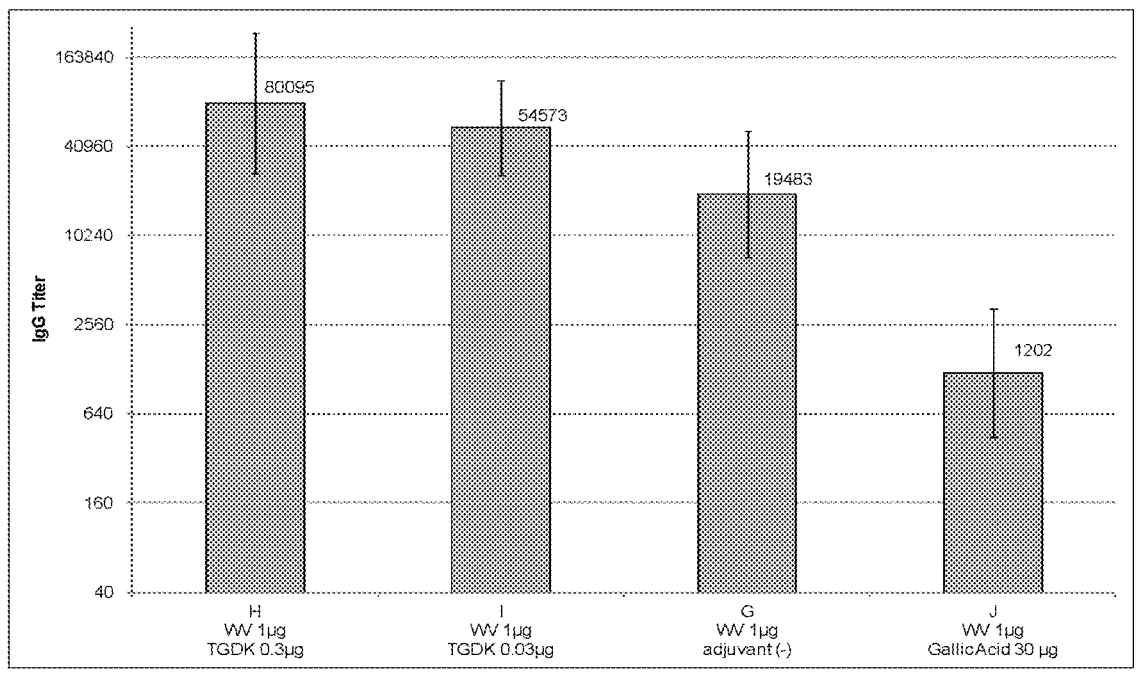
FIG. 4 shows the B/Texas/2/2013 strain-specific IgG antibody titer of an inactivated whole-virus antigen administration group.

FIGS. 3 and 4 show results of inactivated whole-virus antigen administration groups (H to J). It was found that as in the split antigens, the addition of 0.03 or 0.3 μg of TGDK per dose to the inactivated whole-virus antigens increased IgG titers for both the strains, whereas the addition of gallic acid provided an IgG titer for the A/California/07/2009 strain at substantially the same level as in the adjuvant non-addition group, and decreased an IgG titer for the B/Texas/2/2013 strain. Thus, results similar to those of the split antigens were obtained in the inactivated whole-virus antigens. However, the effect of increasing IgG titers by the addition of TGDK is smaller for the inactivated whole-virus antigens than for the split antigens. This is because the inactivated whole-virus antigens themselves have high immunogenicity. It was confirmed that TGDK can exert adjuvant activity in transnasal administration for both of two types of antigens (split antigen and inactivated whole particle antigen) different in immunogenicity.

Figure 5:
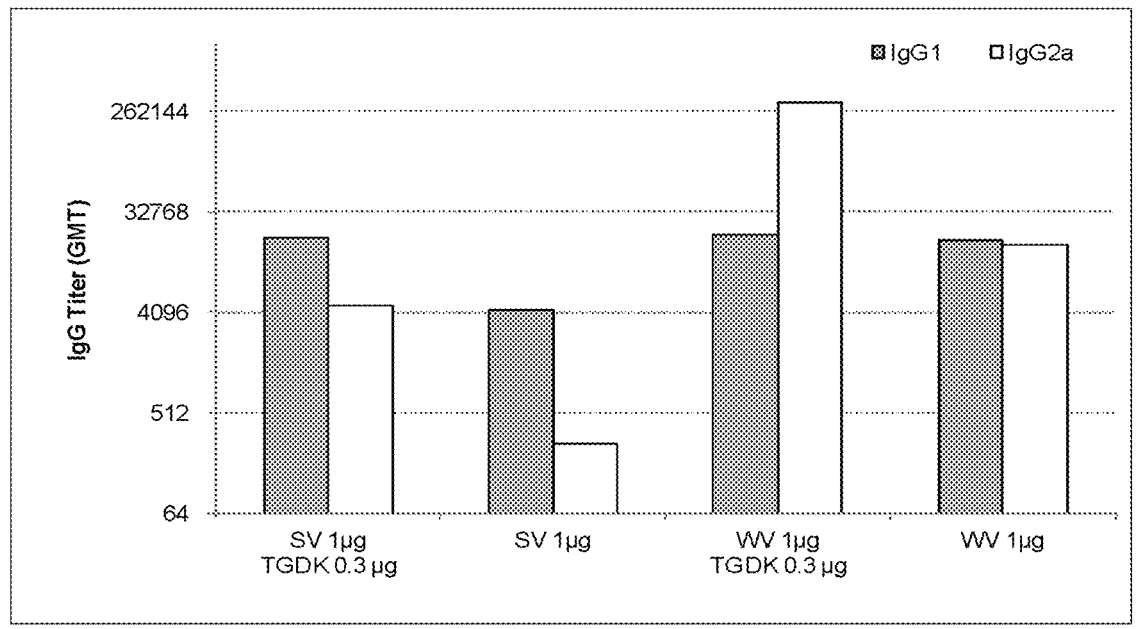
FIG. 5 shows the geometric mean values of B/Texas/2/2013 strain-specific IgG1 and IgG2a antibody titers in each group.

FIG. 5 shows the geometric mean titers (GMT) of IgG1 and IgG2a in each group. As seen therefrom, the addition of TGDK markedly elevated an IgG2a titer for both the split antigens and the inactivated whole-virus antigens. IgG2a which is induced by Th1 response is superior in the ability to defend against infection with influenza virus to IgG1 which is induced by Th2 response. Therefore, the addition of TGDK is expected to further increase efficacy.

Reference Example 1

(1) TGDK was evaluated for its adjuvant activity in subcutaneous administration in the test groups of Table 2 using the same antigens as in Example 1. In this evaluation, Alum (manufactured by Thermo Fisher Scientific Inc., Imject Alum) was additionally used as a control, which is a proven adjuvant for subcutaneous administration.

TABLE 2

| Antigen Type/subtype and lineage | Strain | Type of antigen | Dose (μg HA/ strain/shot) | Adjuvant name | Adjuvant Dose (μg/Shot) | Administration route |
|---|---|---|---|---|---|---|
| A/H1N1 B/Victoria | A/California/07/2009 B/Texas/2/2013 | Split | 1 | TGDK | 30 | Subcutaneous |
| A/H1N1 B/Victoria | A/California/07/2009 B/Texas/2/2013 | Split | 1 | TGDK | 3 | Subcutaneous |

TABLE 2-continued

| Antigen | | | | Adjuvant | | Administration route |
|---|---|---|---|---|---|---|
| Type/subtype and lineage | Strain | Type of antigen | Dose (μg HA/ strain/shot) | Adjuvant name | Dose (μg/Shot) | |
| A/H1N1 B/Victoria | A/California/07/2009 B/Texas/2/2013 | Split | 1 | TGDK | 0.3 | Subcutaneous |
| A/H1N1 B/Victoria | A/California/07/2009 B/Texas/2/2013 | Split | 1 | TGDK | 0.03 | Subcutaneous |
| A/H1N1 B/Victoria | A/California/07/2009 B/Texas/2/2013 | Split | 1 | — | — | Subcutaneous |
| A/H1N1 B/Victoria | A/California/07/2009 B/Texas/2/2013 | Split | 1 | Alm | 30 | Subcutaneous |
| A/H1N1 B/Victoria | A/California/07/2009 B/Texas/2/2013 | Whole particles | 1 | Gallic acid | 30 | Subcutaneous |
| A/H1N1 B/Victoria | A/California/07/2009 B/Texas/2/2013 | Whole particles | 1 | — | — | Subcutaneous |

Figure 6:
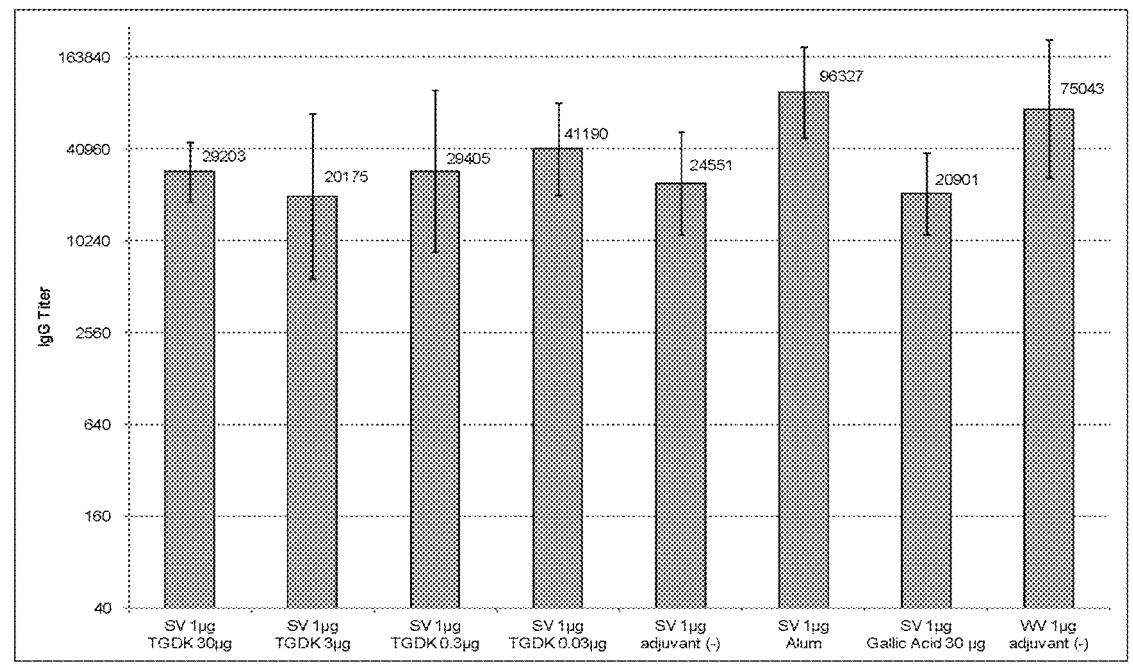
FIG. 6 shows the A/California/07/2009 strain-specific IgG antibody titer.
Figure 7:
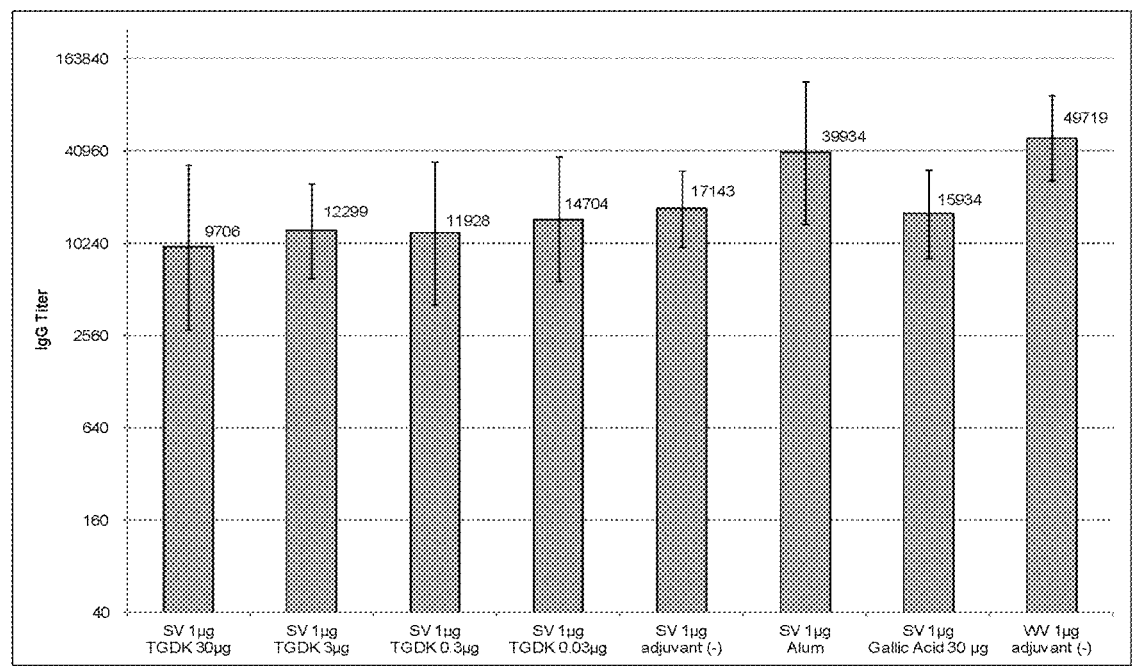
FIG. 7 shows the B/Texas/2/2013 strain-specific IgG antibody titer.

(2) FIG. 6 shows an IgG titer for the A/California/07/2009 strain. FIG. 7 shows an IgG titer for the B/Texas/2/2013 strain. The IgG titers for both the strains in groups added with TGDK were at substantially the same level as in the single administration of the split antigens. Thus, no adjuvant activity was confirmed. Higher IgG titers were exhibited in Alum and inactivated whole-virus administration groups (WV) as compared with the single administration of the split antigens. In subcutaneous administration, the IgG titers for both the strains in a gallic acid addition group were at substantially the same level as in the split antigen single administration group. Neither the gallic acid derivative TGDK nor gallic acid had adjuvant activity in subcutaneous administration.

The invention claimed is:

1. A mucosal vaccine composition, comprising:
   a mucosal adjuvant comprising tetragalloyl-D-lysine dendrimer (TGDK); and
   an immunogen, which is an antigen of influenza virus,
   wherein the TGDK is not chemically bound to the immunogen and present in a free molecular state in the mucosal vaccine composition.

2. The mucosal vaccine composition of claim 1, further comprising:
   a pharmaceutically acceptable carrier.

3. The mucosal vaccine composition of claim 1,
   wherein the immunogen is a whole particle or a split antigen of influenza virus.

4. A mucosal vaccine composition, comprising:
   an inactivated viral mucosal adjuvant comprising tetragalloyl-D-lysine dendrimer (TGDK); and
   an immunogen,
   wherein the immunogen is a whole particle or a split antigen of influenza virus.

5. A method for preparing the mucosal vaccine composition of claim 1, the method comprising:
   mixing the TGDK with the immunogen.

6. A mucosal vaccine therapy, comprising:
   administering an effective amount of the mucosal vaccine composition of claim 1 to a subject in need thereof.

7. The mucosal vaccine composition of claim 1, wherein the TGDK is included in an amount of 0.03 to 30 μg/10 μL.

8. The mucosal vaccine composition of claim 1, wherein the TGDK is included in an amount of 0.03 to 0.3 μg/10 μL.

\* \* \* \* \*

UNITED STATES PATENT AND TRADEMARK OFFICE
CERTIFICATE OF CORRECTION

PATENT NO. : 11,707,521 B2
APPLICATION NO. : 17/279850
DATED : July 25, 2023
INVENTOR(S) : Shogo Misumi et al.

It is certified that error appears in the above-identified patent and that said Letters Patent is hereby corrected as shown below:

In the Claims

In Column 10, Claim 4, Line 26, delete "an inactivated viral" and add "a" therefor.

In Column 10, Claim 4, Line 29, delete the "a" before whole particle and add "an inactivated" therefor.

Signed and Sealed this
Eighth Day of October, 2024

Katherine Kelly Vidal
*Director of the United States Patent and Trademark Office*